(12) United States Patent
Andes et al.

(10) Patent No.: US 6,238,472 B1
(45) Date of Patent: May 29, 2001

(54) METAL OXIDE COATED TITANIUM DIOXIDE LAMELLAS

(75) Inventors: Stephanie Andes, Maintal; Gerd Bauer, Kleinostheim; Günter Brenner, Griesheim; Dieter Brückner, Darmstadt; Michael Schmelz, Kriftel; Andrea Heyland, Ober-Kainsbach; Matthias Kuntz, Seeheim; Karl Osterried, Dieburg; Gerhard Pfaff, Münster, all of (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/230,261

(22) PCT Filed: May 23, 1997

(86) PCT No.: PCT/EP97/02650

§ 371 Date: Mar. 9, 1999

§ 102(e) Date: Mar. 9, 1999

(87) PCT Pub. No.: WO98/53010

PCT Pub. Date: Nov. 26, 1998

(51) Int. Cl.[7] .............. C09C 1/36; C09C 1/00; C09C 1/22; C09C 1/24

(52) U.S. Cl. .......... 106/430; 106/415; 106/437; 106/438; 106/439; 106/441; 106/442; 106/446

(58) Field of Search .................. 106/415, 437, 106/438, 439, 441, 442, 446

(56) References Cited

U.S. PATENT DOCUMENTS

| 3,087,828 | 4/1963 | Linton | 106/291 |
|---|---|---|---|
| 3,395,203 * | 7/1968 | Morita | 106/430 |
| 3,767,443 * | 10/1973 | Clark et al. | 106/430 |
| 3,874,890 | 4/1975 | Bernhard et al. | 106/291 |
| 4,344,987 | 8/1982 | Ostertag et al. | 427/213 |
| 4,744,832 | 5/1988 | Franz et al. | 106/309 |
| 5,009,711 | 4/1991 | Emmert et al. | 106/415 |
| 5,958,125 * | 9/1999 | Schmid et al. | 106/417 |
| 5,985,020 * | 11/1999 | Andes et al. | 106/436 |

FOREIGN PATENT DOCUMENTS

| 1467468 | 12/1968 | (DE). |
|---|---|---|
| 45851 | 2/1982 | (EP). |
| 211351 | 2/1987 | (EP). |
| 307747 | 3/1989 | (EP). |
| 1273230 | 2/1962 | (FR). |
| 2198984 | 4/1974 | (FR). |

OTHER PUBLICATIONS

Derwent Publications, Ltd., London, Great Britain; AN87–039671, XP002037924.
JP61295234A, Dec. 26, 1986 (Sumitumo Chem. Ind.).

* cited by examiner

*Primary Examiner*—Mark L. Bell
*Assistant Examiner*—Michael J. DiVerdi
(74) *Attorney, Agent, or Firm*—Millen White Zelano & Branigan

(57) ABSTRACT

Colored pearl luster pigment consisting of a core of platelet shaped titanium dioxide and one or more layers of other metal oxides or metal oxide hydrates obtainable by solidifying an aqueous solution of a thermally hydrolyzable titanium compound on a continuous belt, detaching the resulting layer, coating the resulting titanium dioxide platelets, with or without drying in between, with one or more other metal oxides or metal oxide hydrates, for example $Fe_2O_3$, $Fe_3O_4$, FeOOH or $Cr_2O_3$, by a wet method, separating, drying and, if desired, calcining the material obtained.

16 Claims, 1 Drawing Sheet

METAL OXIDE COATED TITANIUM DIOXIDE LAMELLAS

Figure 1:
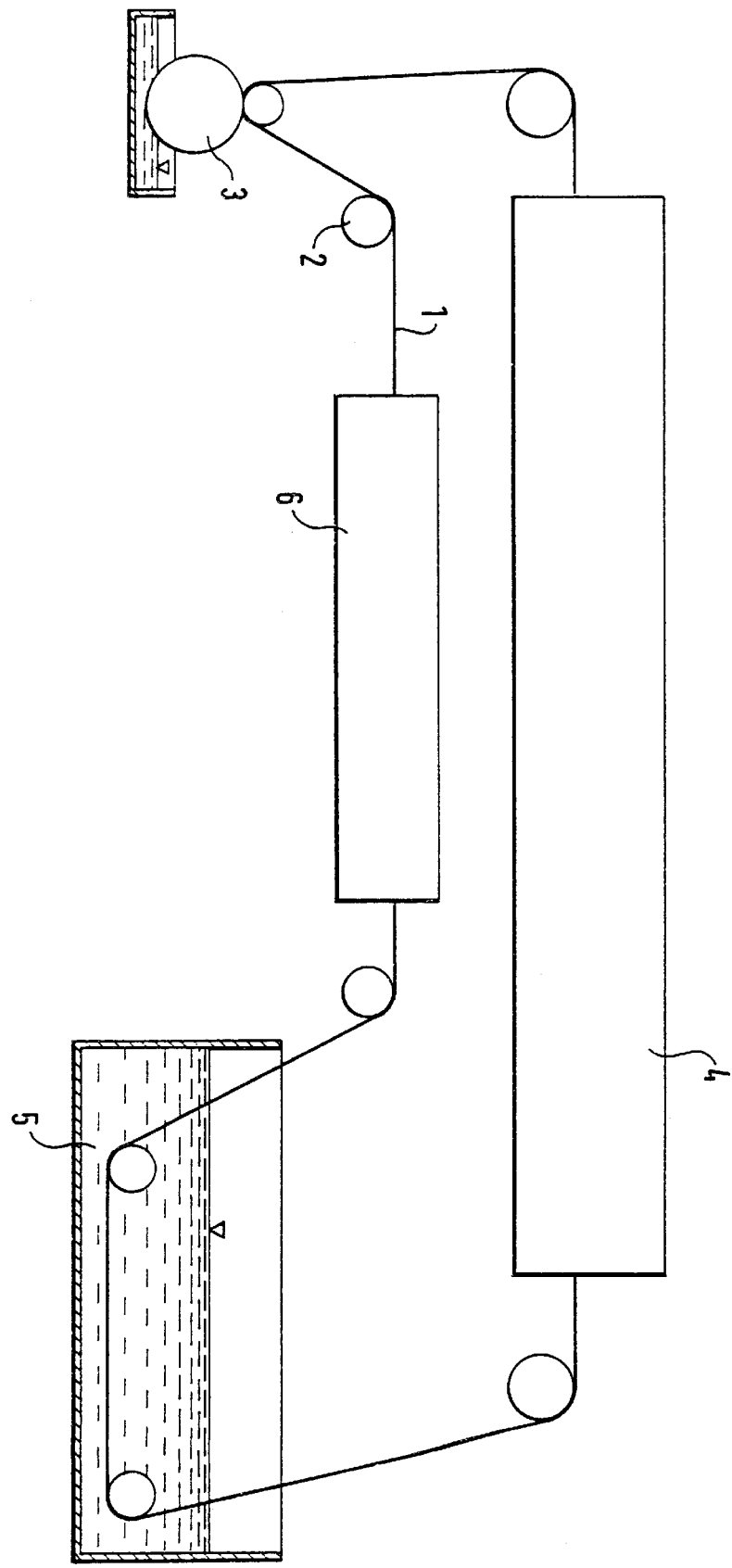

The invention relates to very thin pearl lustre pigments based on metal oxide-coated or metal oxide hydrate-coated platelet shaped titanium dioxide.

Pearl lustre pigments based on mica, which have further metal oxide layers on a titanium dioxide layer, are known. U.S. Pat. Nos. 3,087,828 and 3,087,829 mention aluminium oxide, zirconium oxide, zinc oxide and tin oxide as colourless oxides for a second metal oxide layer and, as oxides which have an intrinsic colour, iron oxide, nickel oxide, cobalt oxide, copper oxide and chromium oxide. The deposition of a second metal oxide on the titanium dioxide hydrate layer leads to a marked stabilization with respect to the photosensitivity of this layer. Iron oxide-containing titanium dioxide pigments, in particular, have been used successfully for many years.

It is described in U.S. Pat. No. 3,087,828 that by deposition of an $Fe_2O_3$—layer on a $TiO_2$ layer gold-coloured mica pigments are obtained which assume a reddish colour shade on calcining.

In U.S. Pat. No. 3,874,890, a process for the preparation of gold-coloured pearl lustre pigments is described in which a mica pigment coated with $TiO_2$ and/or $ZrO_2$ is coated first with iron (II) hydroxide, which is then oxidized to $Fe_2O_3$.

U.S. Pat. No. 4,744,832 describes a pearl lustre pigment based on plateletlike substrates coated with metal oxides, in particular mica, the metal oxide layer containing both titanium and iron and the pigment having a multilayer structure, a layer of pseudobrookite and an iron oxide layer following on a first layer of $TiO_2$ in the rutile form.

Mica pigments are used widely in the printing and coating industries, in cosmetics and in polymer processing. They are distinguished by interference colours and a high lustre. For the formation of extremely thin layers, however, mica pigments are not suitable, since the mica itself, as substrate for the metal oxide layers of the pigment, has a thickness of from 200 to 1200 nm. A further disadvantage is that the thickness of the mica platelets within a certain fraction defined by the platelet size in some cases varies markedly about a mean value. Moreover, mica is a naturally occurring mineral which is contaminated by foreign ions. Moreover, technically highly complex and time-consuming processing steps are required, including, in particular, grinding and classifying.

Pearl lustre pigments based on thick mica platelets and coated with metal oxides have, owing to the thickness of the edge, a marked scatter fraction, especially in the case of relatively fine particle-size distributions below 20 $\mu$m.

As a substitute for mica it has been proposed to use thin glass flakes which are obtained by rolling of a glass melt with subsequent grinding. Indeed, interference pigments based on such materials exhibit colour effects superior to those of conventional, mica-based pigments. Disadvantages, however, are that the glass flakes have a very large average thickness of about 10–15 $\mu$m and a very broad thickness distribution (typically between 4 and 20 $\mu$m), whereas the thickness of interference pigments is typically not more than 3 $\mu$m.

EP 0,384,596 describes a process in which hydrated alkali metal silicate is subjected at temperatures of 480–500° C. to the action of an air jet, forming bubbles with thin walls; the bubbles are subsequently comminuted to give platelet shaped alkali metal silicate substrates with a thickness of less than 3 $\mu$m. However, the process is complex and the thickness distribution of the resulting platelets is relatively broad.

DE 11 36 042 describes a continuous belt method of preparing platelet shaped or glitterlike oxides or oxide hydrates of metals of groups IV and V and of the iron group of the Periodic Table. In this method, a release layer comprising, for example, a silicone coating is first of all applied, if desired, to a continuous belt in order to facilitate the subsequent detachment of the metal oxide layer. Then a liquid film is applied which comprises a solution of a hydrolysable compound of the metal which is to be converted into the desired oxide, and the film is dried and subsequently detached using a vibration device. The layer thickness of the platelets obtained is given as being 0.2 to 2 $\mu$m, although no concrete examples of this are cited.

EP 0,240,952 and EP 0,236,952 propose a continuous belt method of preparing different platelet shaped materials, including silicon dioxide, aluminium oxide and titanium dioxide. In this method, a thin liquid film of defined thickness of a precursor of the platelet shaped material is applied, via a roller system, to a smooth belt; the film is dried and detached from the belt, forming platelet shaped particles. The particles are subsequently, if desired, calcined, ground and classified.

The thickness of the platelets obtained in accordance with the method described in EP 0 240 952 is relatively well defined, since the film is applied very uniformly, via a roller system, to the continuous belt, for example. The layer thickness of the platelets is given in the examples as being 0.3 to 3.0 $\mu$m. According to Example 1, a first roller is wetted with the precursor used by immersing this roller partially into a stock container which is filled with the precursor. The film is tranferred from this roller to a second, co-rotating roller which is in very close contact with the first roller. Finally, the film is rolled off from the second roller onto the continuous belt.

Disadvantages, however, are the use of very expensive precursor materials and, in particular, the increased requirements in terms of workplace safety which must be applied when organometallic compounds are used. The complete chemical conversion of the precursor into the desired layer material requires, in general, strong heating of the film and of the belt material. In addition to the considerable thermal stress which this places on the belt material, the high energy consumption and the restriction on the process speed are highly disadvantageous for the economy of the method.

WO 93/08 237 describes plateletlike pigments consisting of a platelet shaped matrix comprising silicon dioxide, which may contain soluble or insoluble colourants and which is covered with one or more reflecting layers of metal oxides or metals. The platelet shaped matrix is prepared by solidification of waterglass on a continuous belt.

DE 1 273 098 describes the preparation of a mother-of-pearl pigment by vapour deposition of ZnS, $MgF_2$, ZnO, $CaF_2$ and $TiO_2$ films onto a continuous belt. This process, however, like the process described in U.S. Pat. No. 4,879,140 in which platelet shaped pigments with Si and $SiO_2$ layers are obtained by plasma deposition from $SiH_4$ and $SiCl_4$, is associated with very high expenditure on apparatus.

Despite numerous attempts, it has not hitherto been possible to develop any economic process for preparing very thin platelet shaped titanium dioxide pigments having a layer thickness of less than 500 nm.

The object of the invention is to provide highly lustrous pearl lustre titanium dioxide-containing pigments having a layer thickness of less than 500 nm and a layer-thickness tolerance of less than 10%.

This object is achieved in accordance with the invention by a pearl lustre pigment having a multilayer structure, where, on a core of platelet shaped titanium dioxide, there follows a layer of another metal oxide or metal oxide hydrate, obtainable by solidifying an aqueous solution of a thermally hydrolysable titanium compound on a continuous belt, detaching the resulting layer, coating the resulting titanium dioxide platelets, without drying in between, with another metal oxide by a wet method, separating, drying and, if desired, calcining the material obtained.

The other metal oxide or metal oxide hydrate which is applied to the titanium dioxide is $Fe_2O_3$, $Fe_3O_4$, FeOOH, $Cr_2O_3$, CuO, $Ce_2O_3$, $Al_2O_3$, $SiO_2$, $BiVO_4$, $NiTiO_3$, $CoTiO_3$ and also antimony-doped, fluorine-doped or indium-doped tin oxide.

In a particular embodiment of the novel pigment, on the 2nd layer of another metal oxide or metal oxide hydrate is additionally present a 3rd layer of a further metal oxide or metal oxide hydrate. This further metal oxide or metal oxide hydrate is aluminium oxide or aluminium oxide hydrate, silicon dioxide or silicon dioxide hydrate, $Fe_2O_3$, $Fe_3O_4$, FeOOH, $ZrO_2$, $Cr_2O_3$ as well as antimony-doped, fluorine-doped or indium-doped tin oxide.

The aqueous solution of a thermally hydrolysable titanium compound for the preparation of the titanium dioxide platelets on the continuous belt is preferably an aqueous titanium tetrachloride solution.

The concentration of the titanium salt in these solutions is 7 to 30% by weight, preferably 8 to 15% by weight.

This object is additionally achieved in accordance with the invention by a process for preparing the novel pigments, in which an aqueous solution of a thermally hydrolysable titanium compound is applied as a thin film to a continuous belt the liquid film is solidified by drying, during the course of which the titanium dioxide is developed from the precursor by means of a chemical reaction, the resulting layer is subsequently detached from the belt and washed, the titanium dioxide platelets obtained, with or without drying in between, are suspended in water and coated with another metal oxide and, if desired, with further metal oxides, the coated titanium dioxide platelets are separated out from the aqueous suspension, dried and, if desired, calcined.

Additionally, the coating of the titanium dioxide platelets, after drying in between, can also be carried out with metal oxides or metal oxide hydrates, for example, in a fluidized bed reactor by means of gas-phase coating, it being possible, for example, to use the processes for the preparation of pearl lustre pigments proposed in EP 0,045,851 and EP 0,106,235.

The invention moreover relates to the use of the pigments according to the invention for pigmenting paints, printing inks, plastics, cosmetics and glazes for ceramics and glass.

For this purpose, mixtures with commercially available pigments, for example inorganic and organic absorption pigments, metal effect pigments and LCP pigments, can also be employed.

The novel pigments are based on plateletlike titanium dioxide. These platelets have a thickness of between 10 nm and 500 nm, preferably between 40 and 150 nm. The extent in the two other dimensions is between 2 and 200 μm and in particular between 5 and 50 μm.

The layer of another metal oxide which is applied to the titanium dioxide platelets has a thickness of 5 to 300 nm, preferably between 5 and 150 nm.

The novel pigments are prepared in a three-stage process. In the first stage, platelet shaped titanium dioxide particles are prepared with the aid of a continuous belt.

BRIEF DEDESCRIPTION OF DRAWINGS

FIG. 1 shows the belt method of producing the instant particles.

First of all, the belt method will be explained with reference to FIG. 1.

The continuous belt 1, which is guided via a roller system 2, passes through an applicator unit 3 in which it is coated with a thin film of the precursor.

Suitable applicator units which can be employed are roller applicators and also flow-type units. The belt speed is between 2 and 400 m/min, preferably 5–200 m/min.

In order to achieve uniform wetting of the plastic belt it is expedient to add a commercially available wetting agent to the coating solution or to activate the surface of the belt by flame treatment, corona treatment or ionization.

The coated belt subsequently passes through a drying section 4 in which the layer is dried at temperatures between 30 and 200° C. As dryers it is possible, for example, to employ commercially available infrared, circulating-air jet and UV dryers.

After passing through the drying section, the belt is passed through the detachment baths 5 containing an appropriate detachment medium, for example deionized water, where the dried layer is removed from the belt. The detachment procedure is supported by additional devices, for example jets, brushes or ultrasound.

In a subsequent dryer 6, the belt is dried before being coated again.

The continuous belt should be made from a chemically and thermally resistant plastic in order to ensure an adequate service life and high drying temperatures. Suitable materials for the belt include polyethylene terephthalate (PET) or other polyesters and polyacrylates.

The film width is typically between a few centimeters and two or more meters. The thickness is between 10 μm and a few millimeters, these two parameters being optimized in respect of the particular requirements.

Further details of continuous belt methods are known from U.S. Pat. No. 3,138,475, EP 0 240 952 and WO 93/08 237.

In a second process stage, the titanium dioxide platelets detached from the belt are coated, without being dried beforehand, with another metal oxide in accordance with a known method.

When coating with haematite ($Fe_2O_3$), the starting materials can be either iron(III) salts, as is described, for example, in U.S. Pat. No. 3,987,828 and U.S. 3,087,829, or iron(II) salts, as described in U.S. Pat. No. 3,874,890, the initially formed coating of iron(II) hydroxide being oxidized to iron(III) oxide hydrate. Iron(III) salts are preferably used as starting materials. For this purpose, an iron(III) chloride solution is metered into an aqueous suspension of the titanium dioxide platelets at a temperature from 60 to 90° C. and at a pH from 2.5 to 4.5. The pH is kept constant by simultaneous addition of 32% sodium hydroxide solution. After working up and drying at 110° C. a red pigment is obtained.

Coating with magnetite ($Fe_3O_4$) is carried out by hydrolysis of an iron(II) salt solution, for example iron(II) sulphate, at a pH of 8.0 in the presence of potassium nitrate. The particular precipitation examples are described in EP 0,659,843. A black pigment is obtained after working up and drying at 100° C.

Coating of the titanium dioxide platelets with yellow FeO(OH) in the goethite modification is also preferred. In this case, an aqueous $FeSO_4$ solution is metered into a suspension of the titanium dioxide platelets in a nitrogen atmosphere at 70° C. The pH is then adjusted to 4 using a 10% $Na_2CO_3$ solution and oxygen is passed into the suspension. After working up and drying at 110° C. a yellow pigment is obtained. With regard to the precise precipitation conditions reference is made to EP 0,659,843.

For better adhesion of the iron oxide layers to the titanium dioxide platelets it is expedient to apply a tin oxide layer first. In this method, an $SnCl_4$ solution treated with hydrochloric acid is metered into the suspension of the titanium dioxide platelets, which is adjusted to a pH of 1.8, and the pH is kept constant by simultaneous addition of 32% sodium hydroxide solution. After the precipitation of the tin dioxide hydrate layer, coating with an iron oxide hydrate can then immediately follow.

Another metal oxide which is preferably deposited on the titanium dioxide platelets is chromium oxide.

The deposition can easily be effected by means of thermal hydrolysis, which occurs in the volatilization of ammonia from an aqueous solution of a hexaminechromium(III) derivative, or by thermal hydrolysis of a chromium salt solution which is buffered with borax. Coating with chromium oxide is described in U.S. Pat. Nos. 3,087,828 and 3,087,829.

The novel pigments do not have to be calcined in every case. For certain applications drying at temperatures of 110° C. is sufficient. If the pigment is calcined, temperatures between 400° C. and 1000° C. are set, the preferred range being between 400° C. and 700° C.

The novel pigment can in addition be coated with firmly adhering inorganic or organic colorants of low solubility. It is preferred to use colour lakes and, in particular, aluminium colour lakes. To this end an aluminium hydroxide coat is applied by precipitation and in a second step is laked with a colour lake. The process is described in more detail in DE 24 29 762 and DE 29 28 287.

Also preferred is an additional coating with complex salt pigments, especially cyanoferrate complexes, for example Prussian blue and Turnbull's blue, as is described in EP 0 141 173 and DE 23 13 332.

The novel pigment can also be coated with organic dyes and, in particular, with phthalocyanine or metal phthalocyanine and/or indanthrene dyes according to DE 40 09 567. For this purpose a suspension of the pigment in a solution of the dye is prepared, and this suspension is then brought together with a solvent in which the dye is of low or zero solubility.

For an additional coating it is also possible, furthermore, to employ metal chalcogenides or metal chalcogenide hydrates and carbon black.

It is additionally possible to subject the pigments to an aftercoating or aftertreatment which further increases the light stability, weathering resistance and chemical stability or facilitates the handling of the pigment, especially its incorporation into different media. Examples of suitable aftercoating techniques are those described, for example, in DE-C 22 15 191, DE-A 31 51 354, DE-A 32 35 017 or DE-A 33 34 598. Owing to the fact that the properties of the novel pigments are already very good without these additional measures, these optional additionally applied substances make up only from about 0 to 5% by weight, in particular from about 0 to 3% by weight, of the overall pigment.

In terms of the thickness, the novel pigments represent the ideal state which is the most which can be achieved with pearl lustre pigments, since they consist solely of optically functional layers and are devoid of an otherwise customary support material, for example mica or glass flakes, which makes no contribution to the optical effect. Owing to the thickness of the mica, mica pigments possess a thickness which, for a given thickness of the functional layers, is greater by a factor of up to 25. In terms of the technical applications this results in intrinsic advantages which can be achieved by no other conventional pearl lustre pigment. For example, paint layers can be made thinner and the quantity of pigment required can be reduced since, owing to the absence of the support material "filler", the pigments are more optically active.

The examples given below are intended to illustrate the invention without limiting it.

EXAMPLE 1

A circulating belt of polyethylene terephthalate (width: 0.3 m, speed: 20 m/min) is coated with a 20% titanium tetrachloride solution by means of a counter-rotating applicator roll. The coating solution contains 0.3% by weight of surfactant (DISPERSE-AYD W-28, Manufacturer: DANIEL PRODUCTS COMPANY). The aqueous film on the belt is dried in a drying section by subjecting it to hot air at 70° C. and the layer formed is detached from the belt in a detachment basin filled with deionized water. The platelet shaped titanium dioxide particles are filtered and washed with deionized water. The platelets have a silvery lustre and a layer thickness of 100±10 nm. For coating with another metal oxide, they are redispersed in deionized water. 2 l of the dispersion (solids content: 15 g of $TiO_2$) are heated to 75° C. and adjusted with dilute hydrochloric acid to a pH of 1.8.

4.3 g of $SnCl_4.5H_2O$ are dissolved in 29 ml of HCl, and the solution is made up to 290 ml with distilled water and stirred for 10 minutes.

The $SnCl_4$ solution is added to the $TiO_2$ suspension at a rate of 3 ml/min, during which the pH is kept constant at 1.8 with 32% NaOH solution. Following the coating with $SnO_2$, the suspension is stirred at a constant temperature and constant pH for 15 minutes.

The pH is then adjusted to 3.0 using 32% NaOH solution and an aqueous 8% iron(III) chloride solution is metered in at a rate of 3 ml/min, the pH being kept constant by simultaneous addition of the NaOH solution. The $FeCl_3$ addition is continued until the desired interference colour is achieved. The pigment obtained is filtered off, washed with deionized water and dried at 110° C. for 12 hours. The pigment has the desired interference colour and a red body colour.

What is claimed is:

1. A colored pearl luster pigment, comprising a core of platelet shaped titanium dioxide and coated thereon one or more layers of at least one metal oxide or metal oxide hydrate other than a titanium oxide; prepared by a process comprising solidifying an aqueous solution of a thermally hydrolysable titanium compound on a continuous belt, detaching the resulting layer to provide titanium dioxide platelets, coating the resulting titanium dioxide platelets, without drying in between, with at least one metal oxide or metal oxide hydrate other than a titanium oxide by a wet method, and separating, drying, and optionally, calcining the material obtained.

2. A pearl luster pigment according to claim 1, wherein the at least one layer of metal oxide or metal oxide hydrate is $Fe_2O_3$, $Fe_3O_4$, FeOOH or $Cr_2O_3$.

3. A process for preparing the pearl luster pigment according to claim 1, which comprises:

applying an aqueous solution of a thermally hydrolysable titanium compound as a thin film to a continuous belt, solidifying the film on the continuous belt by drying, during the course of which the titanium dioxide is developed from the solution by means of a chemical reaction, detaching the resulting layer from the belt to obtain titanium dioxide platelets, suspending the titanium dioxide platelets, without drying in between, in water and coating them with one or more metal oxides or metal oxide hydrates other than a titanium oxide, and separating the coated titanium dioxide platelets out from the aqueous suspension, drying them, and optionally, calcining them.

4. A process according to claim 3, wherein the aqueous solution of a thermally hydrolysable titanium compound is an aqueous titanium tetrachloride solution.

5. A process according to claim 3, wherein the metal oxide or metal oxide hydrate employed is $Fe_2O_3$, $Fe_3O_4$, FeOOH and $Cr_2O_3$.

6. A process according to claim 3 wherein the coated titanium dioxide platelets separated from the suspension are dried at a temperature from 110 to 150° C.

7. A process according to claim 3 wherein the dried coated titanium dioxide platelets separated from the suspension are calcined at a temperature from 400 to 700° C.

8. A process according to claim 3 wherein the at least one metal oxide or metal oxide hydrate layer is applied to the titanium dioxide platelets in a fluidized-bed reactor by CVD.

9. A paint, printing ink, plastic or cosmetic composition which is pigmented with a pigment according to claim 1.

10. A composition according to claim 9 which additionally comprises another pigment.

11. A pigment according to 1 wherein the at least one layer of metal oxide or metal oxide hydrate is $Fe_2O_3$, $Fe_3O_4$, FeOOH, $Cr_2O_3$, CuO, $Ce_2O_3$, $Al_2O_3$, $SiO_2$, $BiVO_4$, $NiTiO_3$, $CoTiO_3$ or antimony-doped, fluorine-doped or indium-doped tin oxide.

12. A process according to claim 3, wherein at least one layer of metal oxide or metal oxide hydrate is $Fe_2O_3$, $Fe_3O_4$, FeOOH, $Cr_2O_3$, CuO, $Ce_2O_3$, $Al_2O_3$, $SiO_2$, $BiVO_4$, $NiTiO_3$, $CoTiO_3$ or antimony-doped, fluorine-doped or indium-doped tin oxide.

13. The pigment of claim 1, wherein the pigment has a layer thickness of less than 500 nm and a layer-thickness tolerance of less than 10%.

14. The pigment of claim 1, wherein the pigment has at least two layers of different metal oxides or metal oxide hydrates other than titanium dioxide.

15. The process of claim 3, wherein the pigment produced has a layer thickness of less than 500 nm and a layer-thickness tolerance of less than 10%.

16. The process of claim 3, wherein the pigment produced has at least two layers of different metal oxides or metal oxide hydrates other than titanium dioxide.

* * * * *